United States Patent [19]

Drake

[11] Patent Number: 4,555,155
[45] Date of Patent: Nov. 26, 1985

[54] BIOELECTRODE CONNECTOR

[75] Inventor: Gerald E. Drake, Menomonie, Wis.

[73] Assignee: Minnesota Mining and Manufacturing Company, St. Paul, Minn.

[21] Appl. No.: 555,643

[22] Filed: Nov. 28, 1983

[51] Int. Cl.⁴ .............................................. H01R 9/07
[52] U.S. Cl. ........................... 339/61 R; 339/176 MF; 339/253 R
[58] Field of Search ................. 339/97 C, 75 R, 59 R, 339/61 R, 91 R, 260, 261, 176 MF, 17 F, 253 R

[56] References Cited

U.S. PATENT DOCUMENTS

| | | | |
|---|---|---|---|
| 1,521,903 | 1/1925 | Mueller | 339/261 |
| 2,408,045 | 9/1946 | Cottrell | 173/340 |
| 2,503,559 | 4/1950 | Miloche | 173/363 |
| 3,388,369 | 6/1968 | Zalmans | 339/95 R |
| 3,642,008 | 2/1972 | Bolduc | 128/416 |
| 3,740,703 | 6/1973 | Sessions | 339/255 P |
| 3,829,826 | 8/1974 | Brown et al. | 339/255 R |
| 3,842,394 | 10/1974 | Bolduc | 339/75 R |
| 3,976,055 | 8/1976 | Monter et al. | 128/2.06 E |
| 4,061,408 | 12/1977 | Bast et al. | 339/75 R |
| 4,303,293 | 12/1981 | Grunwald | 339/61 M |
| 4,455,057 | 6/1984 | Mariani | 339/97 C |

FOREIGN PATENT DOCUMENTS 2323914 11/1973 Fed. Rep. of Germany ...... 339/176 MF
1292774 3/1962 France .

OTHER PUBLICATIONS

IBM Technical Disclosure Bulletin, vol. 5, No. 11, Apr. 1963 (New York, US); Webb: "Cable Connector", pp. 22, 23.

Primary Examiner—John McQuade
Attorney, Agent, or Firm—Donald M. Sell; James A. Smith; Robert W. Hoke, II

[57] ABSTRACT

A bioelectrode connector for connection with an electrode. The connector includes an elongated, conductive lower member connected to an elongated, movable upper member. The free ends of the upper and lower members are adapted to bend and thereby grasp foil-like tabs on electrodes. Means are provided for releasably latching the free ends of the upper and lower members against further movement once the foil-like tabs are grasped.

2 Claims, 12 Drawing Figures

BIOELECTRODE CONNECTOR

BACKGROUND OF THE INVENTION

The present invention relates to connectors for electrodes. More particularly, it relates to an electrode clip for the connection of a lead cable to a monitoring electrode which, in turn, is secured to a patient.

The physiological functioning of the human or animal body results in certain electrical phenomena. Such phenomena are monitored, for example, by electrocardiographic instrumentation. The instrumentation is typically connected to the body by a lead cable, a connector and an electrode. The lead cables are connected to the instrumentation. The electrodes are applied to the skin. The cables and electrodes are typically interconnected by the connectors.

The electrodes may be connected to the skin by a suction cup, aided by an electrically conductive gel or cream, or they may be glued or taped to the patient's body. The electrode is typically provided with a male pin or male snap fastener. The female portion of the snap is fastened to the connector and is intended to mechanically couple with the male portion. Several different types of cable fasteners are used to couple electrical impulses from the electrode on the patient's body to a cable connected to an electrocardiograph or other monitoring device. The object of all such monitoring electrodes and related connectors is to insure a good electrical and mechanical connection between the skin of the patient and the lead cable.

For example, U.S. Pat. No. 3,740,703 discloses what is referred to as a terminal clip for connecting a lead conductor to an electrode for making electrical connection to skin. The electrode includes what is referred to as a button type male terminal. The clip includes a spring and is constructed to engage the terminal by relative lateral movement of portions of the clip transverse to the axis of the button terminal. Another spring connector is disclosed in U.S. Pat. No. 3,829,826. There, a male snap fastener is held in contact with the cable fastener by a spring. The fastener is said to be small enough to allow shielding of the cable right up to the skin.

U.S. Pat. No. 3,976,055 discloses another electrode for sensing electrocardiograph signals. In FIG. 3, the central conductor has been press fitted into a conventional snap fastener. In FIG. 2, two central conductors are shown connected to an impedance meter by a pair of "alligator" clips.

U.S. Pat. No. 4,303,293 discloses another electrode clip. The clip is formed of resilient plastic material such as polypropylene. Through a series of jaws and living hinges, the electrode clip is secured to what is referred to as an electrode stud on an electrode. The electrode stud, as shown and described, is a traditional male pin or male snap fastener. Hence, the patient is drawn to another type of male and female connector.

The prior devices have concentrated on mechanically adapting both the electrode and the connector to provide a good electrical connection there between. This has been done for two major reasons. First, the strength of the mechanical connection is tested every time the patient moves. Second, the electrical phenomena being monitored is relatively faint. The electrical connection must be quite good to satisfactorily transmit the electrical phenomena to the lead cable and to the monitoring instrumentation.

Where the connector alone has been concentrated on for providing an adequate mechanical and electrical connection between the electrode and the lead cable, the resultant connector has included various clamps, jaws and levers. For example, the connector disclosed in U.S. Pat. No. 4,061,408 includes a pivotally mounted lever for opening and closing the connector.

SUMMARY OF THE INVENTION

According to the present invention, there is provided a relatively small, lightweight bioelectrode connector for use with monitoring instrumentation. The connector includes an elongated, conductive lower member connected to an elongated, movable upper member. The free ends of the upper and lower members are adapted to grasp foil-like tabs on monitoring electrodes. Means are provided for releasably latching the free ends of the upper and lower members against further movement once the foil-like tabs are grasped.

The connector securely connects a planar electrode to a lead cable without the need for male and female parts. As a result, the construction of the electrode is simplified, and the integrity of the mechanical and the electrical connection is maintained.

BRIEF DESCRIPTION OF THE DRAWINGS

Other advantages of the invention will become apparent from the following drawings wherein like numerals refer to like parts, the accompanying description and the appended claims.

DETAILED DESCRIPTION

Figure 1:
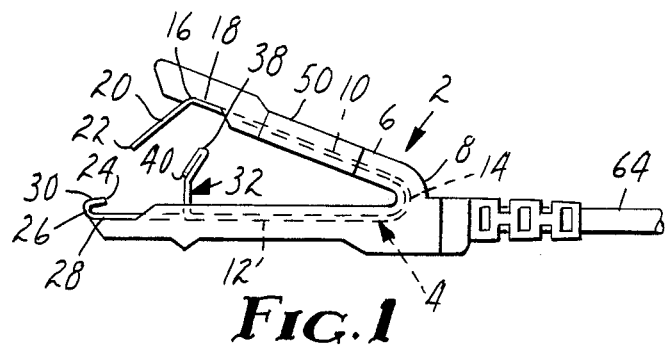
FIG. 1 is a side elevational view of the preferred embodiment of a bioelectrode connector of the present invention in the open position.
Figure 2:
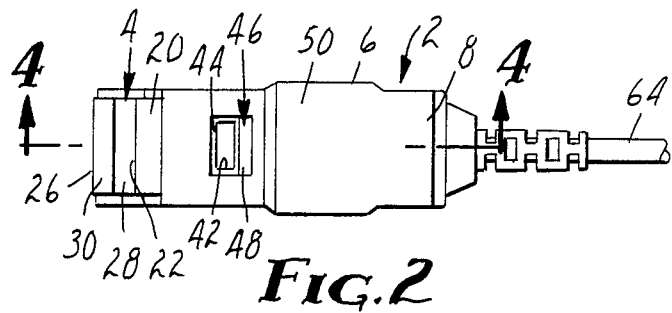
FIG. 2 is a top elevational view of the connector of FIG. 1.
Figure 3:
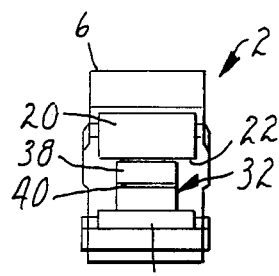
FIG. 3 is an end view of the connector of FIG. 1 as seen from the left of FIG. 1.
Figure 7:
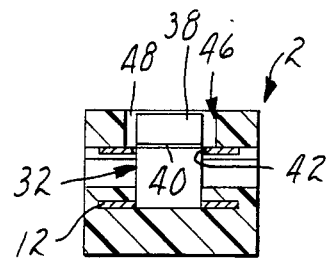
FIG. 7 is an enlarged sectional view of the connector of FIG. 1 taken along the line 7—7 of FIG. 6.

Referring to FIGS. 1-7 and more particularly to FIG. 1, the preferred embodiment of a bioelectrode connector 2 of the present invention is shown in a side elevational view. The connector 2 is generally comprised of an electrially conductive, resilient body 4 embedded within a dielectric cover 6. The dielectric cover 6 is preferably comprised of polypropylene and includes a living hinge 8.

The resilient body 4 has a first upper member 10 and a second lower member 12 connected at portion 14. The resilient body 4 is preferably a bright tin plated stamping made of type 301, three-fourths hard stainless steel. The upper member 10 includes a curved portion 16 formed between straight portions 18 and 20. The straight portion 20 terminates one end of the upper member 10 at an edge surface 22. The other end of the upper member 10 of the resilient body 4 is connected to the curved portion 14 of the resilient body 4.

The lower member 12 of the resilient body 4 includes a curved or arcuate portion 26 between straight portions 28 and 30. The straight portion 30 lies in a plane generally parallel with the plane of the straight portion 28 and terminates one end of the lower member 12 at an edge surface 24. The edge surface 24 is generally perpendicular to the planes of the straight portions 28 and 30. The other end of the lower member 12 is connected to the curved portion 14 of the resilient body 4 opposite the straight portion 18 of the upper member 10.

Referring now to FIGS. 1, 2, 3, 4 and 7, the lower member 12 of the resilient body 4 is shown to include a latching member 32. The latching member 32 is shown stamped from the lower member 12, leaving an aperture 34 within the lower member 12. The latching member 32 is bent up approximately perpendicular to the horizontal plane of the lower member 12. The latching member 32 includes a latching guide 38. The latching guide 38 is bent away from the vertical at a curved portion 35 and includes a contact edge surface 40 to aid in the locking of the bioelectrode connector 2 in a manner to be explained.

The upper member 10 of the resilient body 14 has a receiving aperture 42 within the straight portion 18 for receiving the latching member 32 when the bioelectrode connector 2 is pressed closed in a manner to be explained. A portion of the periphery of the aperture 42 comprises a contact surface 44. The surface 44 is adapted to abut the edge surface 40 of the latching guide 38 of the latching member 32 when the bioelectrode connector 2 is pressed closed.

Figure 4:
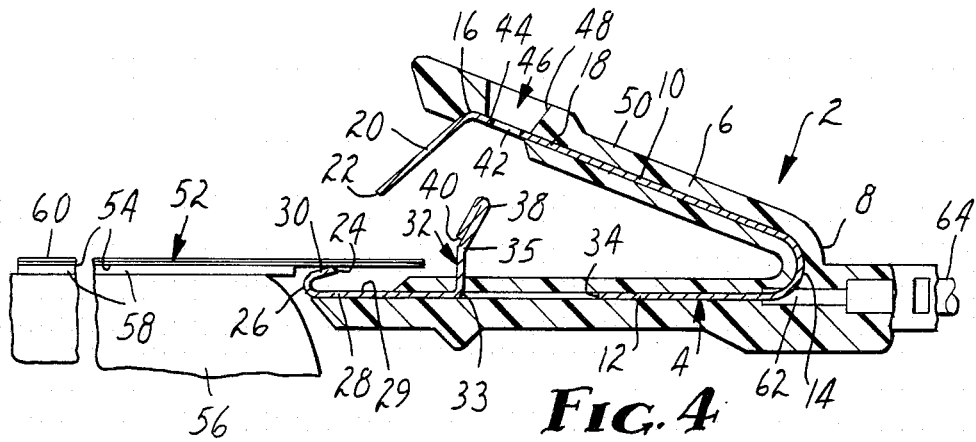
FIG. 4 is an enlarged sectional view of the connector of FIG. 1 taken along the line 4—4 of FIG. 2.

Aligned with the receiving aperture 42 within straight portion 18 is an aperture 46 within the dielectric cover 6. Interior walls 48 of the aperture 46 may be beveled away from the center of the aperture 46 to better accommodate the latching guide 38 as best seen in FIG. 4. A center portion 50 of the dielectric cover 6 may be recessed to facilitate depression of the dielectric cover 6.

The manner in which the bioelectrode connector 2 is securely affixed to an electrode 52 will next be described in reference to FIGS. 4, 5 and 6. FIG. 4 is an enlarged sectional view of the connector 2 taken along the line 4—4 of FIG. 2. It illustrates the connector 2 in the open position. As shown, a conductive layer 54 of the electrode 52 is within the grasp of the bioelectrode connector 2. The electrode 52 is shown for the purpose of illustration to include the conductive layer 54 adhered to a patient's skin 56 by a layer of conductive adhesive 58. The layer 54 may be made of any of a number of thin and deformable, foil-like materials such as tin foil as is well known in the art. The layer 54 is covered with a dielectric material 60 to prevent the electrode 52 from picking up stray electric currents from, among other places, the patient's clothing or surrounding instrumentation. The dielectric covering 60 is typically an adhesive backed paper product entirely covering the conductive layer 54. Similarly, the layer 58 may be comprised of a number of conductive adhesives. For the purposes of illustration, it may be described as comprising an acrylic copolymer adhesive such as is used in medical tapes. Acrylic copolymers, when in thin layers, have proven to be relatively permeable to moisture and permit the exhaustion of perspiration materials that are generated by the skin under the electrode. The layer 58 may be doped with a quantity of metal such as silver as is well known in the art to make the layer 58 conductive. The quantity of silver metal that must be incorporated within the layer 58 may be varied over relatively broad limits. For sake of economy, it is desirable to keep the amount of silver being utilized as low as possible. This may be accomplished by making the particles of silver metal very small and blending them into the adhesive as is well known in the art.

Figure 5:
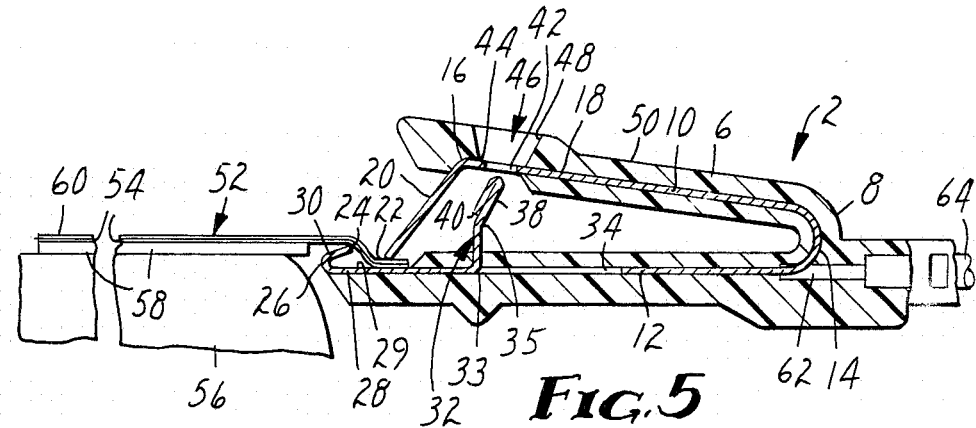
FIG. 5 is an enlarged sectional view identical to FIG. 4 except that the connector of FIG. 1 is shown in the closed, rather than open, position.

FIG. 5 shows the bioelectrode connector 2 pressed down. In the position shown in FIG. 5, the dielectric cover 6 has been depressed moving the edge surface 22 and the arcuate portion 26 generally towards each other and perpendicular to a contact surface 29 on straight portions 28 by flexing the curved portion 14 to the point where the layers 54 and 60 of the electrode 52 are bent past the edge surface 24 and the layer 54 is contacted with the surface 29 of the straight portion 28 by the edge surface 22 of the straight portion 20 of the upper member 10. In this position, the latching guide 38 of the latching member 32 is shown to be aligned with the apertures 42 and 46 within the straight portion 18 of the upper member 10 and the dielectric cover 6, respectively.

Figure 6:
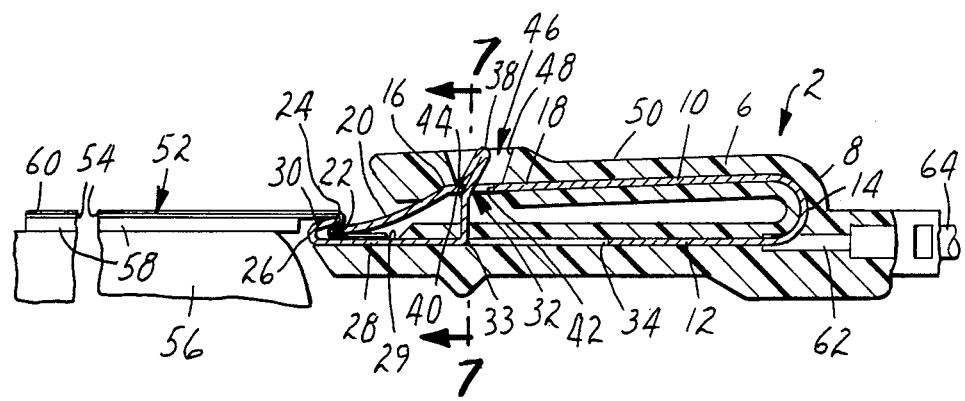
FIG. 6 is an enlarged sectional view identical to FIG. 4 except that the connector of FIG. 1 is shown in the locked, rather than open, position.

As shown in FIG. 6, the dielectric cover 6 is continued to be depressed until the contact surface 44 on the periphery of the aperture 42 is abutted the contact edge surface 40 of the latching guide 38. The movement of the straight portion 18 of the upper member 10 relative to the latching member 32 is facilitated by the latching guide 38. As the straight portion 18 of the upper member 10 approaches the latching member 32, the latching guide 38 directs the surface 40 towards the surface 44. In this process, the latching member 32 is flexed at a curved portion 33 towards the curved portion 14 of the resilient body 4. Once the surface 44 is reached by the surface 40, the latching member 32 snaps back to its upright position thereby abutting the surfaces 40 and 44. The bioelectrode connector 2 is thereby locked on the layers 54 and 60 of the electrode 52 as best shown in FIG. 6 by pinning the layer 54 into intimate contact with the contact surface 29 of the straight portion 28 and by bending the layers 54 and 60 into close proximity with the edge surface 24 of the lower member 12.

Referring to FIG. 6, the edge surface 22 of the top member 10 is shown slid towards the edge surface 24 of the lower member 12. This is made possible by the resilient nature of the body 4. As the top member 10 of the resilient body 4 is pressed from the position shown in FIG. 5 to the position shown in FIG. 6, the curved portion 16 of the top member 10 flexes to slide the edge surface 22 of the upper member 10 generally towards the edge surface 24 of the lower member 12 to tightly bend the top layers 54 and 60 of the electrode 52 into an "S" shape there between. The result is a very secure attachment of the electrode 52 to the connector 2.

Although the lower member 12 has been shown and described to preferably include the straight portion 30, it need not. Depending upon the thickness of the electrode 52 being grasped, the straight portion 30 may be shortened or even eliminated without adversely affecting the integrity of the mechanical and electrical connection. Similarly, depending upon the width of the electrode 52, the straight portion 20 of the upper member 10 may be lengthened to tightly grasp the electrode 52. As long as the layer 54 of the electrode 52 is bent into close proximity with the edge surface 24 and pinned into intimate contact with the contact surface 29, a good mechanical and electrical connection between the bioelectrode connectors and the electrode 52 will result.

The electrode 52 may be released from the bioelectrode connector 2 by reversing the process. The aperture 46 within the dielectric cover 6 is sufficiently large to allow access to the latching guide 38 of the latching member 32. By pressing against the latching guide 38, the latching member 32 may be flexed at the curved portion 33 towards the curved portion 14 of the resilient body 4 to separate surfaces 40 and 44. This, in turn, allows the curved portion 14 of the resilient body 4 and the living hinge 8 of dielectric cover 6 to return the upper member 10 of the resilient body 4 to its open position. The bioelectrode 52 is thereby released.

Once connected, electrical phenomena picked up from the surface 56 being monitored is transmitted through the conductive adhesive 58 to the conductive layer 54. The electrical phenomena passes through the layer 54, and the lower member 12 of the resilient body 4 to the electrical connector 62. In the preferred embodiment, where the resilient body is comprised of the bright tin plated stamping made of type 301, three-fourths hard stainless steel, the electrical phenomena can also pass through the upper member 10 of the resilient body 4 to the electrical connector 62 except for the presence of the dielectric cover 60 or the conductive layer 54. In this embodiment, the bioelectrode connector 2 can be attached to the electrode 52 as shown in FIGS. 4, 5, and 6, or the connector 52 can be reversed or turned upside down relative to the electrode 52 without adverse affect on the ability of the connector 52 to adequately pass the electrical phenomena there through. By reversal or turned upside down it is meant that the dielectric cover 60, rather than the conductive layer 54, is bent around the edge surface 24 so that the conductive layer 54 is contacted by the edge surface 22 of the upper member 10, rather than the edge surface 24 of the lower member 12. For the purpose of illustration, an electrical connector 62 may be soldered at one end to the lower member 12 of the resilient body 4 and crimped at the other end around a lead cable 64 to pass the electrical phenomena there through. The lead cable 64, in turn, may be connected to any number of monitoring instruments including electrocardiographic instrumentation to monitor the signal being transmitted.

Figure 8:
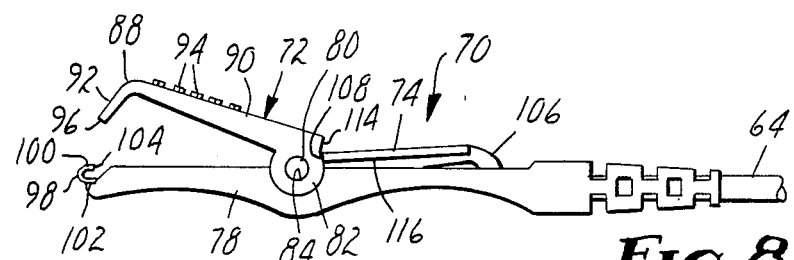
FIG. 8 is a side elevational view of an alternative embodiment of the bioelectrode connector of the present invention in the open position.
Figure 9:
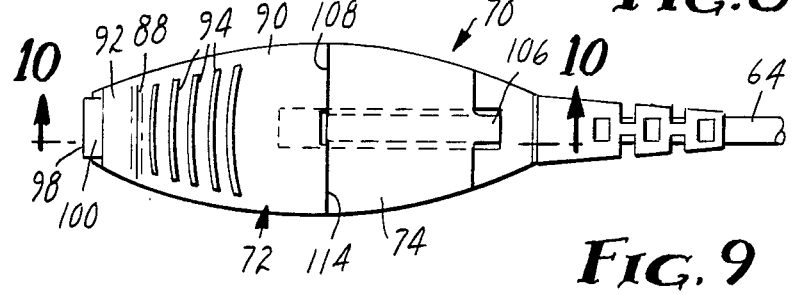
FIG. 9 is a top elevational view of the connector of FIG. 8.

An alternative embodiment of the bioelectrode connector of the present invention is shown in FIGS. 8-12. Referring first to FIG. 8, a bioelectrode connector 70 is shown in a side elevational view. The connector 2 is generally comprised of a pivotally-mounted lever arm 72, a spring-actuated latching member 74 and an electrically conductive, lower member 76 embedded within a dielectric cover 78. The lever arm 72 and the latching member 74 are comprised of a dielectric material, preferably polypropylene.

Figure 12:
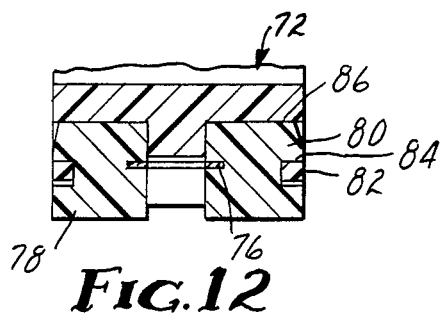
FIG. 12 is an enlarged sectional view of the connector of FIG. 8 taken along the line 12—12 of FIG. 10.

The lever arm 72 is pivotally mounted on the dielectric cover by retaining members 80. The retaining members 80 are best shown in FIG. 12. The lever arm 72, the retaining members 80 and the dielectric cover 78 are preferably comprised of polypropylene. The lever arm 72 includes a pair of mounting portions 82 each having an aperture there through defining a mounting surface 84. The lever arm 72 is mounted on the dielectric cover 78 by flexing the mounting portions 82 generally apart and locating the retaining members 80 within the apertures to contact the mounting surfaces 84 with the end portions 86 of the retaining members 80. This is commonly referred to as a snap fit.

The lever arm 72 includes a curved portion 88 formed between straight portions 90 and 92. The straight portion 90 includes a plurality of protuberances 94 to facilitate use of the connector 70 in a manner to be explained. The straight portion 92 terminates the lever arm 72 at an edge surface 96.

The electrically conductive, lower member 76 includes a curved portion 98 between straight portions 100 and 102. The straight portion 100 lies in a plane generally parallel with the straight portion 102 and terminates one end of the lower member 76 at an edge surface 104. The edge surface 104 is generally perpendicular to the planes of the straight portions 100 and 102. The other end of the lower member 76 is connected to the electrical connector 62 and the lead cable 64 in a manner similar to the embodiment shown in FIGS. 1–7.

The spring-actuated latching member 74 is connected at one end to the dielectric cover 78 by a hinge 106. The hinge 106 is preferably comprised of polypropylene and forms what is generally referred to as a "living hinge" between the latching member 74 and the dielectric cover 78. The other end of the latching member 74 terminates at an edge surface 108.

Figure 10:
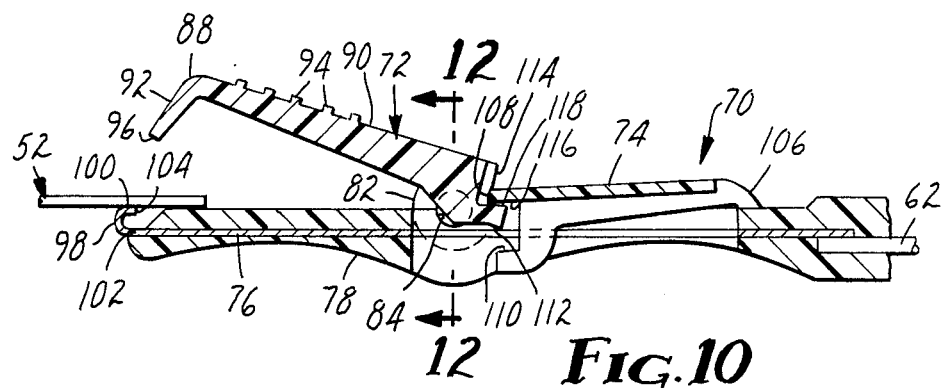
FIG. 10 is an enlarged sectional view of the connector of FIG. 8 taken along the line 10—10 of FIG. 9.

The manner in which the bioelectrode connector 70 is securely affixed to the electrode 52 will next be described in reference to FIGS. 10 and 11. FIG. 10 is an enlarged sectional view of the connector 70 taken along the line 10—10 of FIG. 9. It illustrates the connector 70 in the open position. As shown, the electrode 52 is inserted generally between the edge surface 96 of the lever arm 72 and the edge surface 104 of the lower member 76.

Figure 11:
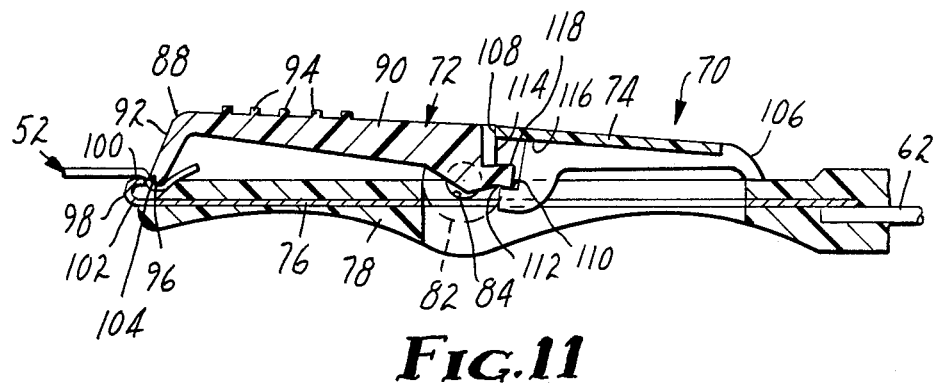
FIG. 11 is an enlarged sectional view identical to FIG. 10 except that the connector of FIG. 8 is shown in the closed, rather than the open, position.

FIG. 11 illustrates the lever arm 72 fully depressed and the bioelectrode connector 70 locked onto the electrode 52. This is accomplished by the user pressing generally downward on the protuberances 94 causing the edge surface 96 to generally approach the edge surface 104. Thus, in turn, bends the electrode 52 between the edge surfaces 96 and 104 and results in a very secure attachment of the electrode 52 to the connector 70 similar to the attachment to the connector 2 described earlier.

The lever arm 72 is held in the position shown in FIG. 11 by the spring-actuated latching member 74. As the lever arm 72 is depressed, the hinge 106 moves the edge surface 108 generally upward until a surface 110 of the latching member 74 contacts a surface 112 of the lever arm 72. This happens when the surface 108 of the latching member 74 is juxtaposed an end portion 114 of the lever arm 72. Once the lever arm 72 is depressed or closed, the lever arm 72 is prevented from returning to the open position shown in FIG. 10 by the surface 108 of the latching member 74 abutting the end portion 114 of the lever arm 72. In this manner, the electrode 52 is grasped and held by the connector 70.

The electrode 52 can be released from the connector 70 by depressing the latching member 74. This forces a surface 116 of the latching member 74 against a surface 118 of the lever arm 72 which, in turn, rotates the lever arm 72 back to the open position.

As shown and described, the bioelectrode conductor of the present invention provides a very safe and reliable mechanical and electrical connection to the electrode. It is extremely lightweight and easy to use.

What is claimed is:

1. A bioelectrode connector adapted for connection with a monitoring electrode having a thin, conductive, deformable tab comprising generally parallel first and second major surfaces, the connector comprising:
    a. an elongate first member having an end portion terminating at a generally transverse, plane edge surface;
    b. an elongate, electrically conductive second member having a contact surface and an arcuate end portion extending from the contact surface and terminating at a generally transverse, plane edge surface overlying and spaced apart from the contact surface;
    c. means for attaching the members opposite the end portions to afford relative movement of the end portions generally perpendicular to the contact surface from an open position with the end portions spaced apart to a closed position with the edge surface of the first member pinning the tab into intimate engagement with the contact surface and bending a portion of the tab adjacent the edge surface of the first member into close proximity with the edge surface of the second member;
    d. means for biasing the end portions in the open position to afford insertion of the tab therebetween; and
    e. means for releasably latching the end portions in the closed position, comprising a latch having a first end portion connected to the second member and a second end portion including means for contacting the first member when the end portion of the first member is in the closed position and for locking the end portion of the first member in the closed position.

2. The connector recited in claim 1 wherein the means for biasing the end portions in the open position comprises a living hinge comprised of polypropylene.

* * * * *